United States Patent [19]

Chibata et al.

[11] 4,415,504

[45] Nov. 15, 1983

[54] P-HYDROXYPHENYLGLYCINE.α-PHENYLETHANESULFONATE, PROCESS FOR PRODUCTION THEREOF AND UTILIZATION THEREOF IN RESOLUTION OF P-HYDROXYPHENYLGLYCINE

[75] Inventors: Ichiro Chibata, Suita; Shigeki Yamada, Toyonaka; Chikara Hongo, Osaka; Ryuzo Yoshioka, Kaizuka, all of Japan

[73] Assignee: Tanabe Seiyaku Co., Ltd., Osaka, Japan

[21] Appl. No.: 416,338

[22] Filed: Sep. 9, 1982

[30] Foreign Application Priority Data

Sep. 21, 1981 [JP] Japan .................. 56-150047
Sep. 21, 1981 [JP] Japan .................. 56-150048

[51] Int. Cl.³ .......................................... C07C 143/26
[52] U.S. Cl. .......................... 260/501.12; 260/505 P; 562/401
[58] Field of Search ............ 260/501.12, 505 P; 562/401

[56] References Cited

U.S. PATENT DOCUMENTS

| | | | |
|---|---|---|---|
| 3,933,902 | 1/1976 | Watanabe et al. | 260/501.12 |
| 3,994,962 | 11/1976 | Shirai et al. | 260/501.12 |
| 4,016,205 | 4/1977 | Kariyone et al. | 260/501.12 |
| 4,115,439 | 9/1978 | Aoki et al. | 260/501.12 |
| 4,233,456 | 11/1980 | Schmand et al. | 260/501.12 |
| 4,309,362 | 1/1982 | Chibata et al. | 260/501.12 |

OTHER PUBLICATIONS

Yamada et al., Chem. Abst., vol. 90, #138,159y (1979).

*Primary Examiner*—James H. Reamer
*Attorney, Agent, or Firm*—Jordan B. Bierman; Linda Bierman

[57] ABSTRACT p-Hydroxyphenylglycine.α-phenylethanesulfonate which is useful for the production of optically active p-hydroxyphenylglycine and optically active α-phenylethanesulfonic acid is disclosed. p-Hydroxyphenylglycine.α-phenylethanesulfonate is produced by either reacting DL-p-hydroxyphenylglycine with optically active α-phenylethanesulfonic acid or reacting (±)-α-phentylethanesulfonic acid with optically active p-hydroxyphenylglycine to form two diastereomers of DL-p-hydroxyphenylglycine optically active α-phenylethanesulfonate or optically active p-hydroxyphenylglycine (±)-α-phenylethanesulfonate, and isolating one diastereomer according to the difference between solubilities of the diastereomers, optionally, combining selective crystallization of one diastereomer and epimerization of another diastereomer in the case of reaction of DL-p-hydroxyphenylglycine and optically active α-phenylethanesulfonic acid. This reaction is utilized in the resolution of p-hydroxyphenylglycine or α-phenylethanesulfonic acid by deacidifying the resulting diastereomer.

32 Claims, No Drawings

P-HYDROXYPHENYLGLYCINE.α-PHENYLE-THANESULFONATE, PROCESS FOR PRODUCTION THEREOF AND UTILIZATION THEREOF IN RESOLUTION OF P-HYDROXYPHENYLGLYCINE

The present invention relates to a novel salt of p-hydroxyphenylglycine, i.e., p-hydroxyphenylglycine-α-phenylethanesulfonate, particularly, a salt of optically active p-hydroxyphenylglycine with optically active α-phenylethanesulfonate, a process for production thereof and the utilization of the process in the optical resolution of p-hydroxyphenylglycine.

Optically active p-hydroxyphenylglycine is a very useful compound. For example, D-p-hydroxyphenylglycine is an important starting material in the production of a semisynthetic penicillin or a semisynthetic cephalosporin and L-p-hydroxyphenylglycine is useful in the treatment of ischemic heart diseases, heart-failure, diabetes and the like (Japanese Patent Laid Open Publication No. 41432/1977).

Since p-hydroxyphenylglycine does not exist in nature, it is produced exclusively by synthesis. However, synthesized p-hydroxyphenylglycine is obtained in the form of the DL-isomer and therefore, in order to obtain the optically active isomer thereof, the optical resolution of the DL-isomer is required.

Various chemical methods of resolving the DL-isomer have been known in the prior art. For example, DL-p-hydroxyphenylglycine is converted into its N-benzyloxycarbonyl derivative, N-chloroacetyl derivative or N-benzoyl derivative and then the resulting derivative is treated with a resolving agent such as quinine, dehydroabietylamine or optically active phenethylamine to resolve the DL-isomer (J. Chem. Soc. (c), 1971, 1920–1922; Japanese Patent Laid Open Publication Nos. 56946/1974 and 69030/1975). However, in these methods, DL-p-hydroxyphenylglycine should be converted into its acyl derivative and the resolving agent to be used is expensive. In addition, according to these methods, deacylation of the optically active acyl derivative obtained by the resolution is required and this is liable to accompany racemization of the product.

It has been also known that DL-p-hydroxyphenylglycine can be resolved by formation of its salt with d-3-bromocamphor-10-sulfonic acid (Japanese Patent Laid Open Publication No. 32541/1976) or by formation of its salt with d-3-bromocamphor-8-sulfonic acid (Japanese Patent Publication No. 45069/1980). However, the former method is unsuitable for the production of the highly purified D-isomer salt since only the L-isomer salt is crystallizable. In the latter method, the resolving agent to be used, which is derived from a naturally occurring substance, is expensive and somewhat chemically unstable. In addition, when the L-p-hydroxyphenylglycine salt which remains in a reaction mixture without crystallization is racemized to be reused as the starting material in these methods, it should be firstly converted into its free amino acid form since the salt itself is hardly racemized without decomposition of the resolving agent.

Under these circumstances, the present inventors have intensively studied in order to establish an efficient resolution method of DL-p-hydroxyphenylglycine. As the results, the following facts have been found.

(1) p-Hydroxyphenylglycine can be reacted with α-phenylethanesulfonic acid, which can also exist in the optically active isomeric form, in an aqueous solvent to form the novel salt, p-hydroxyphenylglycine.α-phenylethanesulfonate.

(2) When either one of the reactants to be used in the reaction of p-hydroxyphenylglycine and α-phenylethanesulfonic acid is the optically active salt, one of the resulting two diastereomers, i.e. D-p-hydroxyphenylglycine.(+)-α-phenylethanesulfonate or L-p-hydroxyphenylglycine.(−)-α-phenylethanesulfonate is always slightly soluble in a reaction medium and the other is always easily soluble in the medium.

(3) When DL-p-hydroxyphenylglycine is reacted with optically active α-phenylethanesulfonic acid, among the resulting two diastereomers, the easily soluble diastereomer can be directly and rapidly converted into the two diastereomers in water or a aliphatic acid by epimerization. Further, the resulting slightly soluble diastereomer is crystallizable from the mixture of two diastereomer even under the epimerization condition of the easily soluble diastereomer. Furthermore, the crystallized slightly soluble diastereomer is stable without being epimerized even under the epimerization condition of the easily soluble diastereomer.

(4) Thus, optically active α-phenylethanesulfonic acid can be used as a resolving agent in resolution of racemic p-hydroxyphenylglycine and this resolution of p-hydroxyphenylglycine is very useful in the industrial production of optically active p-hydroxyphenylglycine. In addition, optically active p-hydroxyphenylglycine is a very useful resolving agent in the industrial production of optically active α-phenylethanesulfonic acid.

Besides, it has been known that (±)-α-phenylethanesulfonic acid is a strong acid compound produced by brominating (±)-α-phenethyl alcohol and then sulfonating the resulting (±)-α-phenethylbromide but, as a resolution method of (±)-α-phenylethanesulfonic acid, only that using strychnine as the resolving agent has hitherto been known in the prior art (J. Chem. Soc., 1159 (1927)).

One object of the present invention is to provide a resolution method of DL-p-hydroxyphenylglycine using optically active α-phenylethanesulfonic acid as a resolving agent.

Another object of the present invention is to provide the novel salt, p-hydroxyphenylglycine.α-phenylethanesulfonate, particularly, optically active p-hydroxyphenylglycine.optically active α-phenylethanesulfonate, which is useful for the production of optically active p-hydroxyphenylglycine.

Still another object of the present invention is to provide a process for producing the novel salt, particularly, a process for selectively producing the slightly soluble diastereomer of optically active p-hydroxyphenylglycine.α-phenylethanesulfonate.

Still another object of the present invention is to provide a resolution method of (±)-α-phenylethanesulfonic acid using optically active p-hydroxyphenylglycine as a resolving agent.

These objects as well as other objects and advantages of the present invention will become apparent to those skilled in the art from the following description.

According to the present invention, the salt of optically active p-hydroxyphenylglycine.optically active.α-phenylethanesulfonate can be produced by either reacting DL-p-hydroxphenylglycine with optically active α-phenylethanesulfonic acid or reacting (±)-α-phenylethanesulfonic acid with optically active p-hydroxyphenylglycine in an aqueous solvent to form two diastereomers of DL-p-hydroxyphenylglycine optically active α-phenylethanesulfonate or optically active p-hydroxyphenylglycine. (±)-α-phenylethanesulfonate and then isolating one diastereomer which being the slightly soluble diastereomer (i.e. D-p-hydroxyphenylglycine.(±)-α-phenylethanesulfonate or L-p-hydroxyphenylglycine.(−)-α-phenylethanesulfonate) according to the difference between solubilities of the diastereomers.

This reaction can be utilized in the resolution of p-hydroxyphenylglycine or α-phenylethanesulfonic acid.

That is, DL-p-hydroxyphenylglycine or (±)-α-phenylethanesulfonic acid can be resolved by using optically active α-phenylethanesulfonic acid or optically active p-hydroxyphenylglycine as a resolving agent in the above reaction and separating the resulting slightly soluble diastereomer converting it into the desired optically active p-hydroxyphenylglycine or optically active α-phenylethanesulfonic acid.

DL-p-Hydroxyphenylglycine (hereinafter referred to as DL-HPG) to be used in the present invention may be a mixture of equal amounts of D- and L-isomers, i.e., a racemic mixture, or a mixture composed of a larger amount of one isomer and a smaller amount of the other isomer, i.e., a so-called low-purity optically active isomer. For example, DL-HPG may be that obtained by synthesis or a low-purity optically active L- or D-p-hydroxyphenylglycine (hereinafter referred to as L-HPG or D-HPG) such as that remaining in a reaction mixture after resolution of DL-HPG according to a conventional method. DL-HPG may be in the free amino acid form or it may be a salt with an inorganic acid such as hydrochloric acid or sulfuric acid or with an organic acid such as oxylic acid or sulfonic acid.

Optically active p-hydroxyphenylvlycine may be D-HPG, L-HPG or a salt thereof with the above acid.

(±)-α-Phenylethanesulfonic acid (hereinafter referred to as (±)-PES) to be used in the present invention may be in the free acid form or it may be a salt with an alkali metal such as sodium or potassium, an alkaline earth metal such as calcium or magnesium or ammonia. (±)-α-Phenylethanesulfonic acid can be prepared according to the method disclosed in J. Chem. Soc., 1159 (1927) as mentioned above.

Optically active -phenylethanesulfonic acid may be (+)-α-phenylethanesulfonic acid (hereinafter referred to as (+)-PES), (−)-α-phenylethanesulfonic acid (hereinafter referred to as (−)-PES) or a salt thereof with an alkali metal, an alkaline earth metal or ammonia.

In the above reaction, when DL-HPG is reacted with (+)-PES in an aqueous solvent, two diastereomers, i.e., D-p-hydroxyphenylglycine.(+)-α-phenylethanesulfonate (hereinafter referred to as D-HPG.(+)-PES) and L-p-hydroxyphenylglycine.(+)-α-phenylethanesulfonate (hereinafter referred to as L-HPG.(+)-PES), are formed in the reaction mixture. Among two diastereomers, D-HPG.(+)-PES is slightly soluble in the aqueous solvent and L-HPG.(+)-PES is easily soluble and therefore, only D-HPG.(+)-PES is crystallized out of the reaction mixture. In case of using (−)-PES, L-HPG.(−)-PES is formed as the slightly soluble diastereomer and D-HPG.(−)-PES is formed as the easily soluble diastereomer.

When (±)-PES is reacted with L-HPG in an aqueous solvent, two diastereomers, i.e., L-HPG.(+)-PES and L-HPG.(−)-PES are formed in the reaction mixture. Likewise, since L-HPG.(−)-PES is the slightly soluble diastereomer and L-HPG.(+)-PES is the easily soluble diastereomer, L-HPG.(−)-PES is crystallized out and L-HPG (+)-PES remains in the reaction mixture. In case of using D-HPG, D-HPG.(+)-PES is formed as the slightly soluble diastereomer and D-HPG.(−)-PES is formed as the easily soluble diastereomer and therefore, it is possible to crystallize out only D-HPG.(+)-PES from the reaction mixture.

The molar ratio of optically active PES or HPG to DL-HPG or (±)-PES in the above reaction is preferably about 0.5 or more, particularly, about 0.8 to 1.1.

As the aqueous solvent to be used in the above reaction, there can be used, for example, water, a lower alkanol such as methanol or ethanol, acetone, a aliphatic acid such as acetic acid or propionic acid or a mixture thereof. Water is preferred.

The reaction can be carried out, for example, by stirring the reactants (i.e. DL-HPG and otically active PES or (±)-PES and optically active HPG) in the above solvent at room temperature or with warming. Crystallization of the slightly soluble diastereomer formed, D-HPG.(+)-PES or L-HPG.(−)-PES can be readily carried out by cooling or concentration of the reaction mixture or by addition of an organic solvent such as toluene or xylene and the diastereomer of high purity can be obtained. The crystallized slightly soluble diastereomer can be separated from the reaction mixture according to a conventional solid-liquid separation technique such as filtration, centrifugation and the like. If necessary, the slightly soluble diastereomer thus obtained can be subjected of a further treatment such as washing, recrystallization or the like.

Each diastereomer formed in the above reaction is the novel optically pure salt composed of 1 mole of optically active HPG and 1 mole of optically active PES. The physical properties of each diastereomer are shown in Table 1.

TABLE 1

| Salts | m.p. (°C.) | $[\alpha]_D^{25}$ (°(c = 1, CH$_3$OH)) | Solubility (g/100 ml H$_2$O at 20° C. | Elemental analysis | | | |
|---|---|---|---|---|---|---|---|
| | | | | C | H | N | S |
| D-HPG. (+)-PES | 251–252 | −78.9 | 1.05 | 54.39 | 5.51 | 3.99 | 8.78 |
| L-HPG. (−)-PES | 252–253 | +78.8 | 1.05 | 54.39 | 5.46 | 4.00 | 8.89 |
| D-HPG. (−)-PES | 203–204 | −98.5 | 80 | 54.38 | 5.48 | 3.97 | 9.76 |
| L-HPG. (+)-PES | 204–205 | +98.6 | 80 | 54.36 | 5.43 | 4.01 | 9.03 |

In a preferred aspect of the present invention, DL-HPG is reacted with optically active PES to form two diastereomers and epimerization of the easily soluble diastereomer, i.e., L-HPG.(+)-PES or D-HPG. (−)-PES is effected simultaneously with crystallization of the slightly soluble diastereomer, i.e., D-HPG.(+)-PES or L-HPG.(−)-PES. According to this aspect, epimerization of the easily soluble diastereomer proceeds with crystallization of the slightly soluble diastereomer and, since the slightly soluble diastereomer once crystallized is not epimerized, substantially all the diastereomers present in the reaction mixture are converted into the slightly soluble diastereomer and thereby, the slightly soluble diastereomer can be selectively produced. Namely, a second-order asymmetric transformation by selective crystallization of the slightly soluble diastereomer and simultaneous epimerization of the easily soluble diastereomer is effected.

The conditions for epimerization and crystallization are not critical. For example, epimerization can be effected by heating the reactants in the presence of water or by stirring the reactants in a lower fatty acid in the presence of an aliphatic or aromatic aldehyde. Crystallization of the slightly soluble diastereomer can be effected at room temperature or even with heating. Preferably, epimerization is effected under such a condition that the slightly soluble diastereomer formed from the easily soluble diastereomer is crystallized out of the reaction mixture.

When epimerization is effected in the presence of water with heating, a small amount of water is added to the reactants, i.e., DL-HPG and optically active PES and the mixture is heated. The reaction proceeds at about 80° to 160° C., preferably, about 100° to 150° C.

When epimerization is effected in a lower aliphatic acid in the presence of an aliphatic or aromatic aldehyde, the reaction can be carried out in a solvent or without any solvent. In this case, DL-HPG, optically active PES, a lower aliphatic acid, an aldehyde and, if necessary, a solvent are mixed and stirred to proceed epimerization. The order of addition of the reactants are not critical. The reaction can be carried out at room temperature to a reflux temperature of the lower aliphatic acid or the solvent. Particularly, about 50° to 110° C. is preferred.

In either case, since the slightly soluble diastereomer firstly formed by the reaction of DL-HPG and optically active PES is crystallized out of water or a lower aliphatic acid, the epimerization can be effected after separation of the firstly formed slightly soluble diastereomer or it can be effected in a heterogeneous system containing the crystallized slightly soluble diastereomer. Further, a reaction temperature can be lowered in the course of the epimerization process to separate the slightly soluble diastereomer present in the reaction mixture. Furthermore, optionally, the epimerization of the easily soluble diastereomer can be effected in a low concentration followed by crystallization of the slightly soluble diastereomer by cooling. In any case, the reaction readily proceeds.

Examples of the lower fatty acid to be used are fatty acids having 1 to 5 carbon atoms such as formic acid, acetic acid, propionic acid, butyric acid and valeric acid. Particularly, glacial acetic acid is preferred since it can be readily available. The concentration of the lower fatty acid in the reaction mixture is not critical but, usually, the lower fatty acid is used in the concentration of about 50 W/V % or more, preferably, about 80 W/V % or more. It is preferable to use the lower fatty acid in an amount of about 2 to 50 times as much as the total amount of DL-HPG and optically active PES.

Examples of the aldehyde to be used are saturated or unsaturated aliphatic aldehydes such as formaldehyde, acetaldehyde, propionaldehyde, n-butylaldehyde, i-butylaldehyde, acrolein and the like and aromatic aldehydes such as benzaldehyde, salicylaldehyde, p-hydroxybenzaldehyde, nitrobenzaldehyde, anisaldehyde and the like. Particularly, salicylaldehyde and n-butylaldehyde are preferred. It is preferable to use the aldehyde in the molar ratio to DL-HPG optically active PES of 0.01 to 0.2

As the solvent to be optically used in the epimerization, there can be used any solvent which is inert to DL-HPG, the lower aliphatic acid and the aldehyde and can allow to crystallize out the slightly soluble diastereomer therefrom. Examples of the solvent are water, benzene, toluene and the like.

In addition, the above epimerization can be accelerated by using a free amino acid together with DL-HPG. The free amino acid may be that of any kinds and it may be an optically active isomer or a racemic isomer. Further, it may be a mixture of free amino acids. In general, free HPG is preferred since the resulting slightly soluble diastereomer is not contaminated by any different amino acid.

It is preferable to use the free amino acid in the molar ratio to PES of about 0.02 to 0.2.

The slightly soluble diastereomer thus formed is separated from the reaction mixture as mentioned above.

D-HPG.(+)-PES or L-HPG.(−)-PES obtained by the process of the present invention can be readily separated into optically active HPG and optically active PES by a known method such as the treatment with an ion exchange resin or an alkali and thereby, resolution of DL-HPG or (±)-PES can be accomplished. For example, when an aqueous solution of D-HPG.(+)-PES is treated with an alkali (e.g. sodium hydroxyde, potassium hydroxyde, ammonium hydroxyde, etc.) to adjust the pH of the solution to the isoelectric point of HPG, it is separated into D-HPG and (+)-PES and only D-HPG is crystallized out of the solution. Likewise, only L-HPG is crystallized out of an aqueous solution of L-HPG.(−)-PES. The crystallized optically active HPG can be separated from the solution by a conventional solid-liquid separation technique such as filtration to obtain D- or L-HPG. On the other hand, since an alkaline salt of optically pure PES is dissolved in the mother liquid, a solution of optically active PES can be obtained by acidification of the mother liquid. Optically active HPG or the solution of optically active PES thus obtained can be used as the starting material in the process of the present invention.

As mentioned hereinabove, in the resolution of DL-HPG according to the present invention, the desired optically active HPG can be selectively crystallized out in the form of the slightly soluble diastereomer by using (+)-PES or (−)-PES as the resolving agent. Likewise, in the resolution of (±)-PES, the desired optically active PES can be selectively crystallized out in the form of the slightly soluble diastereomer by using D-HPG as the resolving agent. Further, the reaction can be readily carried out by a simple operation in an aqueous solvent. Furthermore, when the epimerization of the easily soluble diastereomer is effected, substantially all DL-HPG can be converted into the desired optically active HPG by a simple operation, whereas, according to a conventional chemical resolution method, only 50 parts of the desired optically active HPG is theoretically obtained from 100 parts of DL-HPG.

Thus, according to the present invention, there is no need to convert DL-HPG into another derivative such as an acyl derivative thereof or to racemize the remaining unnecessary optically active HPG as in a conventional method and therefore, the process of the present invention is very useful in industrial production of optically active HPG. In addition, although optically active PES has hitherto been hardly commercially available even as a chemical reagent, according to the present invention, it can be readily produced on a large scale and therefore, it makes possible to supply optically active PES industrially.

The following examples further illustrate the present invention in detail but are not to be construed to limit the scope thereof.

EXAMPLE 1

L-HPG (16.7 g) was dissolved in an aqueous solution (450 g) containing (±)-PES (19.0 g) with heating. The solution was slowly cooled to room temperature and stirred for 2 hours. The crystals thus formed were filtered off and washed with cold water to give L-HPG.(−)-PES (16.2 g). $[\alpha]_D^{25} +79.0°$ (c=1, CH$_3$OH).

EXAMPLE 2

(1) D-HPG (102.8 g), (±)-PES NH$_4$ (125 g) and conc. sulfuric acid (33.2 g) were dissolved in water (2.2 l) with heating. The solution was stirred at room temperature for 2 hours. The crystals thus formed were filtered off, washed with water and dried to give D-HPG.(+)-PES (95.1 g). $[\alpha]_D^{25} -79.2°$ (c=1, CH$_3$OH).

(2) Methanol (87 ml) was added to D-HPG (+)-PES prepared in the above (1) (29,0 g) and an aqueous sodium hydroxide solution was added to the mixture with stirring to adjust pH to 6. After stirring at room temperature for 2 hours, the mixture was filtered to give D-HPG (13.0 g). $[\alpha]_D^{25} -155.0°$ (c=1, N HCl).

(3) The mother liquid of the above (2) was concentrated to remove methanol and water was added to the concentrate. The resulting mixture was passed through a column of Amberlite IR-120 (H+) and the column was washed with water. The eluent and the washing were combined and concentrated to give 10% solution of (+)-PES (150 g).

EXAMPLE 3

D-HPG (27.6 g), conc. hydrochloric acid (45.3 ml) and water (300 ml) were dissolved in a reaction mixture of (±)-PES (150 g) (prepared by reacting (±)-α-phenylethylbromide (55.5 g) with ammonium sulfate) with heating. The mixture was stirred at 20° C. for 2 hours. The crystals thus formed were filtered off, washed with water and dried to give D-HPG.(+)-PES (23.3 g). $[\alpha]_D^{25} -79.4°$ (c=1, CH$_3$OH).

EXAMPLE 4

DL-HPG (20 g) and conc. hydrochloric acid (11 ml) was dissolved in water (300 ml). To the solution was slowly added a solution of (+)-PES NH$_4$ (24.3 g) in water (200 ml). The mixture was stirred at room temperature for 2 hours. The crystals thus formed were filtered off, washed with water and dried to give D-HPG (+)-PES (19.7 g). $[\alpha]_D^{25} -75.8°$ (c=1, CH$_3$OH).

EXAMPLE 5

(1) DL-HPG HCL (10.0 g) was reacted with (+)-PES NH$_4$ (9.98 g) in water (10 ml) to form two diastereomers of DL-HPG (+)-PES. DL-HPG (0.82 g) was added to the reaction mixture and the mixture was heated in an autoclave at 140° C. for 12 hours. After completion of the reaction, 50% aqueous solution of (+)-PES (1.8 g) and water (10 ml) were added to the reaction mixture and the mixture was stirred at room temperature for 1 hour. The crystals thus formed were filtered off and dried to give D-HPG (+)-PES (17.73 g). $[\alpha]_D^{25} -76.5°$ (c=1, CH$_3$OH), Optical purity 97.3%.

(2) Methanol (44 ml) was added to D-HPG (+)-PES prepared in the above (1) (14.5 g) and an aqueous sodium hydroxide solution was added to the mixture with stirring to adjust pH to 6. The mixture was stirred at room temperature for 2 hours and filtered to give D-HPG (6.5 g). $[\alpha]_D^{25} -158.0°$ (c=1, 1 N HCl), Optical purity 99.8%.

EXAMPLE 6

A mixture of DL-HPG (11.0 g), (−)-PES NH$_4$ (12.2 g), conc. hydrochloric acid (5.1 ml) and water (10 ml) was heated in an autoclave at 120° C. for 23 hours. 50% Aqueous solution of (−)-PES (2.2 g) and water (10 ml) were added to the reaction mixture and the mixture was stirred at room temperature for 1 hour. The crystals thus formed were filtered off and dried to give L-HPG.(−)-PES (20.0 g). $[\alpha]_D^{25} +74.9°$ (c=1, CH$_3$OH), Optical purity 95.6%.

EXAMPLE 7

Methanol (30 ml) was added to D-HPG.(+)-PES prepared in Example 5 (10 g) and the mixture was adjusted to pH 6 by addition of aqueous ammonia with stirring at about 50° C. Stirring was continuted at room temperature for 2 hours. The crystals thus formed were filtered off to give D-HPG (4.51 L g). $[\alpha]_D^{25} -157.9°$ (c=1, 1 N HCl).

The mother liquor was concentrated to dryness and the residue was dried to give (+)-PES NH$_4$ (5.97 g). Conc. sulfuric acid (0.8 ml), salicylaldehyde (0.3 ml) and glacial acetic acid (70 ml) were added to (+)-PES NH$_4$ (5.97 g). DL-HPG (4.74 g) was slowly added to the resulting heterogeneous system with stirring at 100° C. and stirring was continued for 3.5 hours. Additional salicylaldehyde (0.3 ml) was added and stirring was continued at the same temperature for additional 3.5 hours. Acetic acid was distilled off under a reduced pressure. To the residue was added water (10 ml) and the mixture was stirred for 1 hour. The crystals thus formed were filtered off, washed and dried to give D-HPG.(+)-PES (7.62 g). $[\alpha]_D^{25} -75.1°$ (c=1, CH$_3$OH), Optical purity 95.7%.

EXAMPLE 8

Water (300 ml) was added to a mixture of DL-HPG (16.72 g) and 50% aqueous solution of (+)-PES (37.24 g). The resulting mixture was stirred at 40° to 50° C. for 3 hours and further at room temperature for 2 hours. The crystals thus formed was filtered to give D-HPG.(+)-PES (16.74 g). $[\alpha]_D^{25} -74.5°$ (c=1, CH$_3$OH), Optical purity 95.0%.

The mother liquid was concentrated to dryness and the residue was dried to give L-HPG (+)-PES. Glacial acetic acid (60 ml) and salicylaldehyde (0.55 ml) were added to L-HPG (+)-PES and the mixture is stirred at 100° C. for 6 hours. After cooling to room temperature, the crystals formed were filtered off and dried to give D-HPG.(+)-PES (15.9 g). $[\alpha]_D^{25} -74.2°$ (c=1, CH$_3$OH), Optical purity 94.7%.

REFERENCE EXAMPLE (1) According to the method described in J. Chem. Soc., 1159 (1927), (±)-α-phenethyl alcohol (500 g) was brominated and the resulting (±)-α-phenethylbromide was sulfonated. To the reaction mixture were added D-HPG (376 g), conc. hydrochloric acid (620 ml) and water (4 l) and the mixture was heated to form a solution. The solution was stirred at 20° C. for 2 hours. The crystals thus formed were filtered off, washed with water, dried and recrystallized to give pure D-HPG.(+)-PES (290 g). $[\alpha]_D^{25} -78.9°$ (c=1, CH$_3$OH).

(2) D-HPG.(+)-PES prepared in the above (1) was suspended in methanol and the mixture was adjusted to pH 6 by addition of an aqueous sodium hydroxide solution. The mixture was stirred to crystallize out D-HPG. D-HPG was filtered off and the mother liquid is concentrated to remove methanol. Water was added to the concentrate and the mixture was passed through a column of Amberlite IR-120 ($H^{30}$). The eluate was concentrated to give 10% solution of (+)-PES. $[\alpha]_D^{25} +6.2°$ (c=1, $H_2O$).

(3) The same procedure as described in the above (1) was repeated except that the same amount of L-HPG was substituted for D-HPG to give pure L-HPG.(−)-PES. $[\alpha]_D^{25} +78.9°$ (c=1, $CH_3OH$).

(4) L-HPG.(−)-PES prepared in the above (3) was treated as in the above (2) to give 10% solution of (−)-PES. $[\alpha]_D^{25} -6.2°$ (c=1, $H_2O$).

What is claimed is:

1. p-Hydroxyphenylglycine.α-phenylethanesulfonate.

2. The compound according to claim 1 being DL-p-hydroxyphenylglycine.optically active α-phenylethanesulfonate.

3. The compound according to claim 1 being optically active p-hydroxyphenylglycine.(±)-α-phenylethanesulfonate.

4. The compound according to claim 1 being D-p-hydroxyphenylglycine.(+)-α-phenylethanesulfonate.

5. The compound according to claim 1 being L-p-hydroxyphenylglycine.(−)-α-phenylethanesulfonate.

6. A process for producing the optically active p-hydroxyphenylglycine.optically active α-phenylethanesulfonate which comprises reacting DL-p-hydroxyphenylglycine with optically active α-phenylethanesulfonic acid to form two diastereomers of the optically active p-hydroxyphenylglycine.optically active α-phenylethanesulfonate one of which being the easily soluble diastereomer and the other of which being the slightly soluble diastereomer, crystallizing the slightly soluble diastereomer and collecting the crystallized slightly soluble diastereomer.

7. A process according to claim 6, wherein crystallization of the slightly soluble diastereomer is effected under a condition for epimerization of the easily soluble diastereomer.

8. A process according to claim 6 or 7, wherein optically active α-phenylethanesulfonic acid is used in a molar ratio to DL-p-hydroxyphenylglycine of about 0.5 or more.

9. A process according to claim 8, wherein optically active α-phenylethanesulfonic acid is used in a molar ratio to DL-p-hydroxyphenylglycine of about 0.8 to 1.1.

10. A process according to claim 7, wherein the epimerization is effected in the presence of water with heating at 80° to 160° C.

11. A process according to claim 7, wherein the epimerization is effected in the presence of a aliphatic acid and an aliphatic or aromatic aldehyde.

12. A process according to claim 11, wherein the aliphatic acid is that having 1 to 5 carbon atoms.

13. A process according to claim 12, wherein the aliphatic acid is glacial acetic acid.

14. A process according to claim 11, wherein the aliphatic acid is present in a concentration of 50 W/V % or more.

15. A process according to claim 11, wherein the aldehyde is a member selected from the group consisting of formaldehyde, acetaldehyde, propionaldehyde, n-butylaldehyde, i-butylaldehyde, acrolein, benzaldehyde, salicylaldehyde, hydroxybenzaldehyde, nitrobenzaldehyde and anisaldehyde.

16. A process according to claim 15, wherein the aldehyde is salicylaldehyde or n-butylaldehyde.

17. A process according to claim 15, the aldehyde is used in a molar ratio to DL-p-hydroxyphenylglycine.optically active α-phenylethanesulfonic acid of 0.01 to 0.2.

18. A process according to claim 7, wherein the epimerization is effected in the presence of a free amino acid.

19. A process according to claim 18, wherein the free amino acid is used in a molar ratio to optically active α-phenylethanesulfonic acid of about 0.02 to 0.2.

20. A process according to claim 6, wherein the reaction is carried out in an aqueous solvent and collection of the diastereomer is effected according to the difference between solubilities of two diastereomers.

21. A process according to claim 20, wherein the solvent is a member selected from the group consisting of water, methanol, ethanol, acetone, acetic acid, propionic acid and a mixture thereof.

22. A process for producing optically active p-hydroxyphenylglycine which comprises reacting DL-p-hydroxyphenylglycine with optically active α-phenylethanesulfonic acid to form two diastereormers of the optically active p-hydroxyphenylglycine.optically active α-phenylethane sulfonate, epimerizing the easily soluble diastereomer, collecting the crystallized slightly soluble diastereomer and converting the slightly soluble diastereomer into optically active p-hydroxyphenylglycine.

23. A method for resolving DL-p-hydroxyphenylglycine which comprises reacting DL-p-hydroxyphenylglycine with optically active α-phenylethanesulfonic acid to form two diastereomers of DL-p-hydroxyphenylglycine.optically active α-phenylethanesulfonate collecting one diastereomer and converting the diastereomer into optically active p-hydroxyphenylglycine.

24. A method according to claim 23, wherein the reaction is carried out in an aqueous solvent and collection of the diastereomer is effected according to the difference between solubilities of two diastereomers.

25. A method according to claim 24, wherein the solvent is a member selected from the group consisting of water, methanol, ethanol, acetone, acetic acid, propionic acid and a mixture thereof.

26. A method according to claim 24, wherein optically active α-phenylethanesulfonic acid is used in a molar ratio of to DL-p-hydroxyphenylglycine of about 0.5 or more.

27. A method according to claim 26, wherein the molar ratio is about 0.8 to 1.1.

28. A method for resolving (±)-α-phenylethanesulfonic acid which comprises reacting (±)-α-phenylethanesulfonic acid with optically active p-hydroxyphenylglycine to form two diastereomers of optically active p-hydroxyphenylglycine.(±)-α-phenylethanesulfonate, collecting one diastereomer and deacidifying the diastereomer.

29. A method according to claim 28, wherein the reaction is carried out in an aqueous solvent and collection of the diastereomer is effected according to the difference between solubilities of two diastereomers.

30. A method according to claim 29, wherein the solvent is a member selected from the group consisting of water, methanol, ethanol, acetone, acetic acid, propionic acid and a mixture thereof.

31. A method according to claim 29, wherein optically active p-hydroxyphenylglycine is used in a molar ratio to (±)-α-phenylethanesulfonic acid of about 0.5 or more.

32. A method according to claim 31, wherein the molar ratio is about 0.8 to 1.1.

* * * * *